US007500402B2

(12) United States Patent
Pors et al.

(10) Patent No.: US 7,500,402 B2
(45) Date of Patent: Mar. 10, 2009

(54) ULTRASONIC FLOW RATE MEASURING DEVICE

(75) Inventors: Jan Pors, Oud-Bijerland (NL); Jeroen v. d. Berg, Hendrik Ido Ambacht (NL); Marcel Molenaar, Dordrecht (NL); Jankees Hogendoorn, Spijk (NL)

(73) Assignee: Krohne AG, Basel (CH)

( * ) Notice: Subject to any disclaimer, the term of this patent is extended or adjusted under 35 U.S.C. 154(b) by 0 days.

(21) Appl. No.: 11/684,992

(22) Filed: Mar. 12, 2007

(65) Prior Publication Data
US 2007/0227264 A1    Oct. 4, 2007

(30) Foreign Application Priority Data
Mar. 30, 2006    (DE) ................ 10 2006 015 217

(51) Int. Cl.
*G01F 1/66*    (2006.01)

(52) U.S. Cl. .................................................. 73/861.28

(58) Field of Classification Search .............. 73/861.29, 73/861.18, 861.27, 861.28
See application file for complete search history.

(56) References Cited

U.S. PATENT DOCUMENTS

| 4,286,470 | A | * | 9/1981 | Lynnworth ............... 73/861.18 |
| 4,454,767 | A | * | 6/1984 | Shinkai et al. ........... 73/861.18 |
| 4,948,552 | A | | 8/1990 | Mollot et al. |
| 6,397,683 | B1 | | 6/2002 | Hagenmeyer et al. |
| 6,626,049 | B1 | * | 9/2003 | Ao ........................... 73/861.29 |
| 6,883,386 | B2 | | 4/2005 | Osone et al. |

* cited by examiner

*Primary Examiner*—Jewel Thompson
(74) *Attorney, Agent, or Firm*—David S. Safran; Roberts Mlotkowski Safran & Cole, P.C.

(57) ABSTRACT

An ultrasonic flow rate measuring device for measuring the flow rate of a medium flowing through a line (1), with at least one ultrasonic transducer (2) and a guide frame (3) for guiding and holding the ultrasonic transducer (2). An electrical connecting box (12) which has a connection (13) for a cable (14) to the ultrasonic transducer (2) and a connection (15) for a cable (16) to the measuring device electronics is provided. Thus, in a clamp-on ultrasonic flow rate measuring device, simple cabling is achieved.

10 Claims, 5 Drawing Sheets

ULTRASONIC FLOW RATE MEASURING DEVICE

BACKGROUND OF THE INVENTION

1. Field of the Invention

The invention relates to an ultrasonic flow rate measuring device, especially a clamp-on ultrasonic flow rate measuring device, for measuring the flow rate through a line through which a medium flows, with at least one ultrasonic transducer and a guide frame for guiding and holding the ultrasonic transducer.

2. Description of Related Art

Clamp-on ultrasonic flow rate measuring devices are characterized in that they can be used especially easily. In contrast to other ultrasonic flow rate measuring devices which must be permanently integrated into the existing pipeline system by replacing a piece of the pipeline, clamp-on flow rate measurement devices can simply be placed on the outside of a suitable line section of the piping system. The line section to which the clamp-on ultrasonic flow rate measuring device is attached thus becomes more or less a measuring line without the need for its own separate measuring line which must be inserted into the piping system. This makes the use of clamp-on ultrasonic flow rate measuring devices simple and economical.

However, the problem in clamp-on ultrasonic flow rate measurement devices is the correct attachment of the measurement device to the line, especially with respect to the correct arrangement and alignment of the ultrasonic transducers, which in an ultrasonic flow rate measuring device, are generally formed by two ultrasonic transducers located at a distance from one another in the lengthwise direction of the line. In addition to the corresponding problem in the initial attachment of the clamp-on ultrasonic flow rate measuring device to the line, there is the problem that, even for a correctly positioned and aligned measurement device, this state can be lost again when the ultrasonic transducer must be removed from the line, for example, for maintenance purposes.

Especially for clamp-on ultrasonic flow rate measurement devices, the problem is that each ultrasonic transducer is provided with its own cable which connects it to the measurement electronics. This is especially a hindrance in the installation of a clamp-on ultrasonic flow rate measurement device, but also in removal and re-attachment of the clamp-on ultrasonic flow rate measurement device within the framework of maintenance or repair.

SUMMARY OF THE INVENTION

Accordingly, a primary object of the present invention is to devise an ultrasonic flow rate measuring device, especially a clamp-on ultrasonic flow rate measurement device, which can be easily handled with respect to its cabling.

Proceeding from the initially described type of ultrasonic flow rate measuring device, this object is achieved in that there is an electrical connecting box which has a connection for a cable to the ultrasonic transducer and a connection for a cable to the measuring device electronics.

Providing an electrical connecting box in accordance with the invention is advantageous in that the connecting box can be handled together with the guide frame and the ultrasonic transducer, for example, can be removed from the line, without removing the cable from the ultrasonic transducer to the connecting box, while a cable is not connected from the measuring device electronics to the connecting box.

Basically, the connections for a cable to the ultrasonic transducer or for a cable to the measuring device electronics can be made in different ways. According to the preferred development of the invention, it is provided that there is a respective plug-in connection for the connection for a cable to the ultrasonic transducer and/or for the connection for a cable to the measuring device electronics.

It is especially advantageous if the cable to the ultrasonic transducer runs within the guide frame. In this way, there is essentially no risk that this cable will be adversely affected in the handling of the ultrasonic flow rate measuring device, for example, when it is removed from the line.

Handling of the ultrasonic flow rate measuring device is especially simple when, according to a preferred development of the invention, it is provided that the electrical connecting box is attached to the guide frame.

Finally, according to a preferred development of the invention, it is provided that there are two ultrasonic transducers, a separate cable at a time running to each of the ultrasonic transducers from the connecting box, while there is only a single cable to the measurement device electronics. To remove the ultrasonic flow rate measuring device from the line, thus only a single connection need be unclamped, specifically the connection of the cable from the measurement device electronics on the connecting box; this makes handling especially simple, in particular specifically avoids having to handle more than a single cable.

According to a preferred development of the invention, there is a fixing means by which the ultrasonic transducer can be moved onto the line or away from it, and can be fixed on the guide frame or can be unclamped from it.

Thus, there is also a fixing means which assumes two functions, by means of which the ultrasonic transducer can be moved preferably perpendicularly onto the line, and finally, can be pressed against it, in order to ensure good acoustic contact between the ultrasonic transducer and line. With the fixing means, of course, the ultrasonic transducer can be moved away from the line again so that it no longer touches the line. As a second function, the ultrasonic transducer can be fixed on the guide frame and also can be unclamped again from it by the fixing means.

According to a preferred development of the invention, it is provided that the ultrasonic flow rate measuring device can be attached to the line by means of the guide frame. In this connection, on the one hand, it can be provided that attachment takes place directly via the guide frame, but it can also be provided that the guide frame is movably attached, for example, to fastening means which are, for their part, attached to the line.

According to a preferred development of the invention, it is also provided that the fixing means is made and arranged such that the ultrasonic transducer, when moved onto the line, is fixed at the same time on the guide frame, and when moved away from the line, is unclamped at the same time from the guide frame.

Unclamping the ultrasonic transducer from the guide frame in this invention is defined as the ultrasonic transducer remaining attached to the guide frame, preferably captively, but being movable on it. In particular, according to a preferred development of the invention, it is provided that the ultrasonic transducer, in the state released from the guide frame, can be pushed on the guide frame, preferably in its lengthwise direction, and in this connection, is guided by the guide frame.

In this way, the ultrasonic transducer can be pushed within a guide frame attached to the line, for example, in the lengthwise direction of the line, in order to find the correct location for positioning of the ultrasonic transducer. The ultrasonic transducer can then be fixed there on the guide frame, at the same time, movement onto the line taking place so that the ultrasonic transducer finally comes into contact with the line in order to achieve a good acoustic transition between the ultrasonic transducer and the line, and thus, also to the medium flowing through the line.

Basically, the fixing means can be made in various ways in order to have the above described properties. According to a preferred development of the invention, it is provided that the fixing means has a knob which, by its rotation in one direction, moves the ultrasonic transducer onto the line and at the same time fixes it on the guide frame, and by turning it in the other direction, the ultrasonic transducer is moved away from the line and at the same time is unclamped from the guide frame.

According to a preferred development of the invention, it can also be provided that the fixing means fixes the ultrasonic transducer on the guide frame by its clamping the ultrasonic transducer or a clamping means provided on the ultrasonic transducer to the guide frame. Preferably, in this connection, it is provided that the fixing means runs within a guide groove provided in the guide frame and clamping onto the walls of the guide frame which laterally border the groove takes place to fix the ultrasonic transducer.

In this connection, according to a preferred development of the invention, it is fundamentally provided that there is a fixing means on the ultrasonic transducer which interacts with the guide frame such that the ultrasonic transducer can be moved lengthwise in its unclamped state. Here, for example, there can also be a groove in the ultrasonic transducer or in a means provided on the ultrasonic transducer; the groove running in a corresponding counterpart on the guide frame.

According to a preferred development of the invention, it is also provided that the guide frame with the ultrasonic transducer fixed on it can be unclamped from the line and afterwards re-attached to it. This means that the ultrasonic transducer also remains fixed in the guide frame in a predetermined manner in the state of the guide frame removed from the line. This is especially important when, according to a preferred development of the invention, there are two ultrasonic transducers which are each fixed by means of its own fixing means at a predetermined distance from one another on the guide frame, the guide frame in this state being able to be unclamped from the line and afterward re-attachable to it. This is especially associated with the advantage that, after an initial correct alignment of the ultrasonic transducers relative to one another, this arrangement is maintained even after repair or maintenance, for which the ultrasonic transducers must be removed from the line.

The invention is explained in detail below with reference to accompanying the drawings which show preferred embodiments of the invention.

DETAILED DESCRIPTION OF THE INVENTION

Figure 1A:
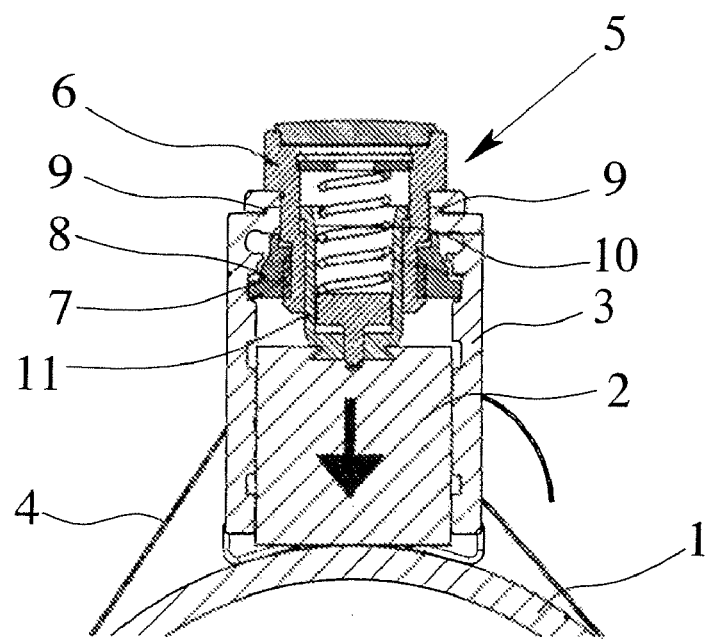
FIGS. 1a & 1b each show a cross section of an ultrasonic flow rate measuring device according to a first preferred embodiment, FIGS. 2a & 2b each show a partial section of the ultrasonic flow rate measuring device according to a first preferred embodiment of the invention in a perspective view.
Figure 1B:
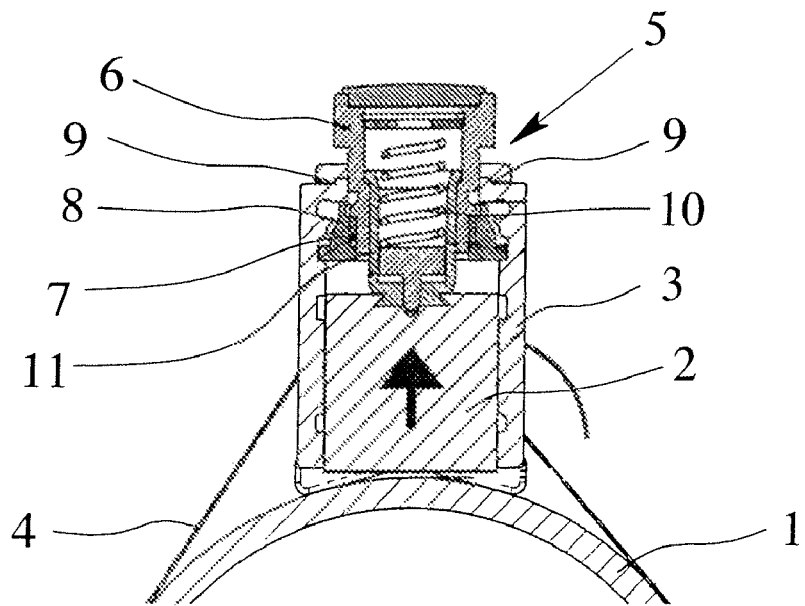

FIGS. 1a & 1b show a clamp-on ultrasonic flow rate measuring device according to a first preferred embodiment of the invention which is mounted on a line 1 through which a medium can flow. The clamp-on ultrasonic flow rate measuring device according to the first preferred embodiment of the invention has an ultrasonic transducer 2 and a guide frame 3 which is used to guide and hold the ultrasonic transducer 2 and is attached by means of a fastening strap 4 to the line 1.

In the clamp-on ultrasonic flow rate measuring device according to the first preferred embodiment of the invention described here, there is a fixing means 5 by means of which the ultrasonic transducer 2 can be moved perpendicularly to the lengthwise axis of the line 1 onto it (FIG. 1a) and likewise perpendicularly to the lengthwise axis of the line 1 away from it (FIG. 1b). At the same time, the fixing means 5 causes fixing of the ultrasonic transducer 2 on the guide frame 3 when moved onto the line 1 while the ultrasonic transducer 2 is unclamped from the guide frame 3 in the movement of the ultrasonic transducer 2 away from the line 1. In this released state, the ultrasonic transducer 2 can then be moved parallel to the lengthwise axis of the line 1, therefore perpendicularly into or out of the plane of these figures of the drawings.

The fixing means has a knob 6 which interacts with a clamping means 8 which is guided via a thread 7 in the guide frame 3 parallel to the lengthwise axis of the line 1. The ultrasonic transducer 2 has its top is attached to the knob 6 so that turning of the knob 6 clockwise or counterclockwise leads to the ultrasonic transducer 2 being pressed onto the line 1 or being lifted off it. The top of the knob 6 has a larger diameter than the middle part of the knob 6 so that the top part of the knob 6 rests on the side walls 9 of the guide frame 3 which border the groove running parallel to the lengthwise axis of the line 1 in the guide frame 2 when fully screw in as shown in FIG. 1a.

When the knob 6 is screwed clockwise into the clamping means 8, it moves the transducer 2 relative to the guide frame 3 so that the fixing means 5 is tensioned, on the one hand, and the clamping means 8 is compressed, on the other hand. Moreover, screwing the knob 6 into the clamping means 8 moves the ultrasonic transducer 2 toward the line 1 so that the ultrasonic transducer 2, as a result, is pressed securely on the line 1; this ensures a good acoustic transition. In this state, the ultrasonic transducer 2 can no longer move, especially not in the lengthwise direction of the guide frame 3.

To ensure high enough contact pressure for attaching the ultrasonic transducer 2 on the line 1 without risking damage to the ultrasonic transducer 2 by pressing onto the line 1, there is a spring 10 within the knob 6. This spring 10 presses upward against the top of the knob 6 and interacts toward the bottom on a spring housing 11 which can be moved in the knob 6, perpendicular to the lengthwise axis of the guide frame 3 and via which the ultrasonic transducer 2 is attached to the fixing means 5. Thus, the spring sets the maximum contact pressure between the transducer 2 and the line 1, since once the contact pressure exceeds the resistance of the spring, the spring will compress relieving the contact pressure by enabling the spring housing 11 to move upward away from the line 1.

Figure 2A:
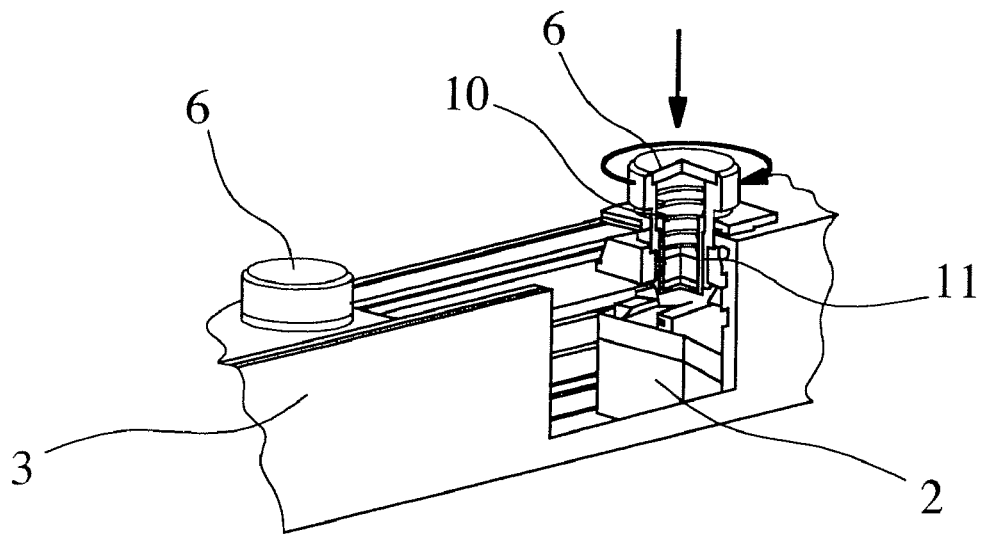
Figure 2B:
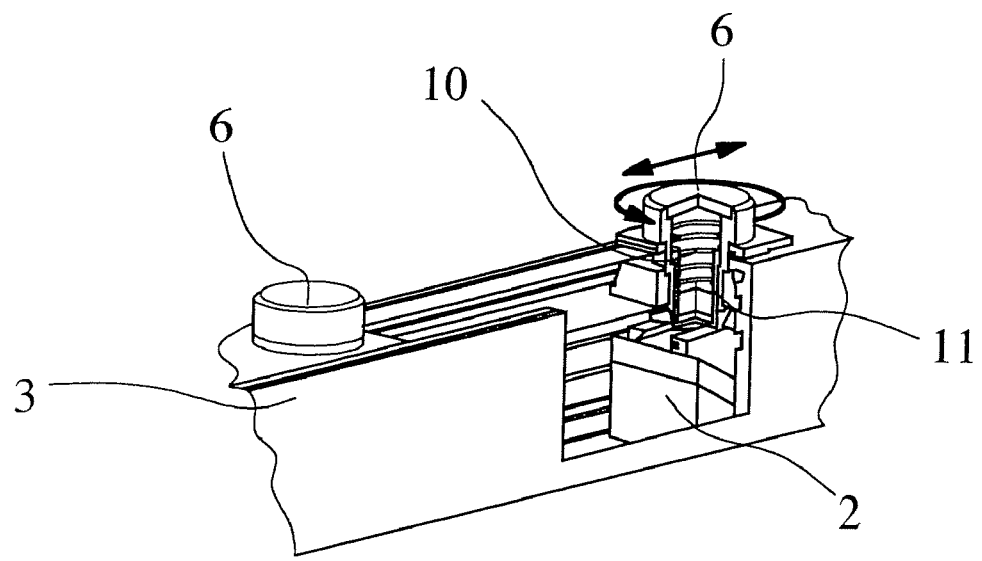

As is apparent from FIGS. 2a & 2b, turning of the knob 6 clockwise leads to fixing of the ultrasonic transducer 2 in the guide frame 3 due to the above noted compression of the clamping means 8, such that movement of the ultrasonic transducer 2 in the lengthwise direction is no longer possible, while the ultrasonic transducer 2 is pressed securely onto the line 1. When the knob is turned counterclockwise the ultrasonic transducer 2 is raised off the line 1 and movement of the ultrasonic transducer 2 in the lengthwise direction of the guide frame 3 is possible, for example, to re-position the ultrasonic transducer 2.

As is likewise apparent from FIGS. 2a & 2b, the clamp-on ultrasonic flow rate measuring device according to the first preferred embodiment of the invention described here has two ultrasonic transducers 2, of the left ultrasonic transducer only the top part of the knob 6 being shown. For two ultrasonic transducers 2 with the clamp-on ultrasonic flow rate measuring device according to the first preferred embodiment of the invention described here, there is the advantage that, after correct positioning of the ultrasonic transducers 2, they can be fixed on the guide frame 3, and the guide frame 3 then can be removed from the line 1 without endangering the correct alignment of the ultrasonic transducers 2 relative to one another.

As a result, such a clamp-on ultrasonic flow rate measuring device is provided which can be easily unclamped from the line 1, for example, for maintenance and repair purposes, without the ultrasonic transducers 2 having to be recalibrated relative to one another in a complex process upon re-attachment to the line 1.

Figure 3:
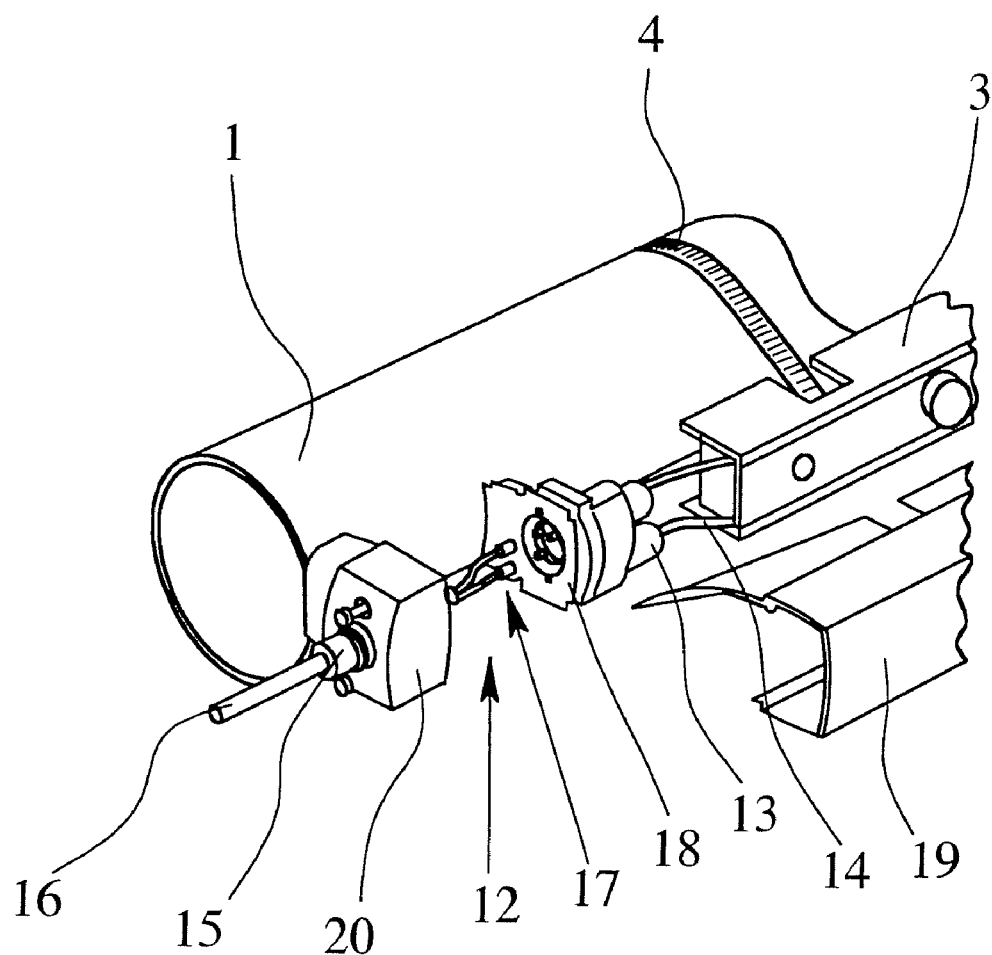
FIG. 3 is a perspective view of an ultrasonic flow rate measuring device according to a second preferred embodiment of the invention with an electric connecting box before its mounting on the guide frame.
Figure 4:
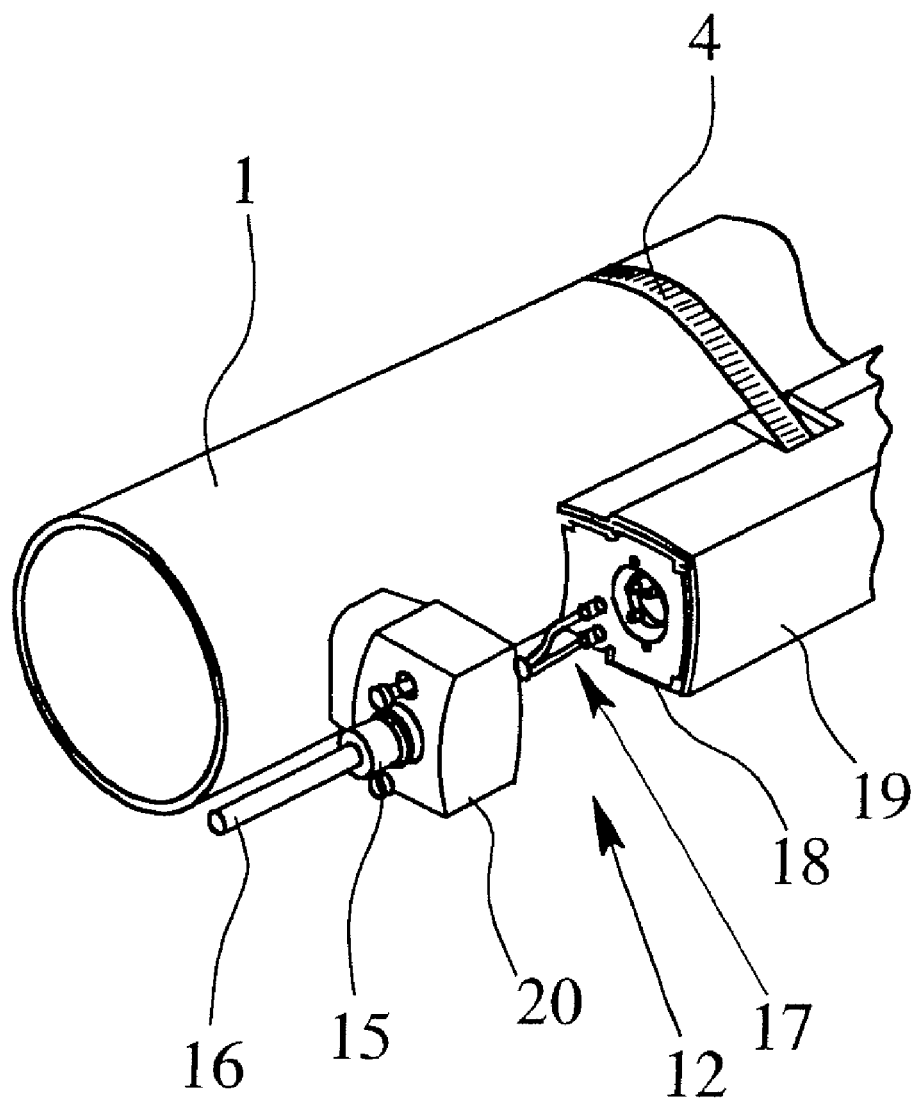
FIG. 4 is a perspective view of an ultrasonic flow rate measuring device according to a second preferred embodiment of the invention with an electric connecting box mounted on the guide frame.
Figure 5:
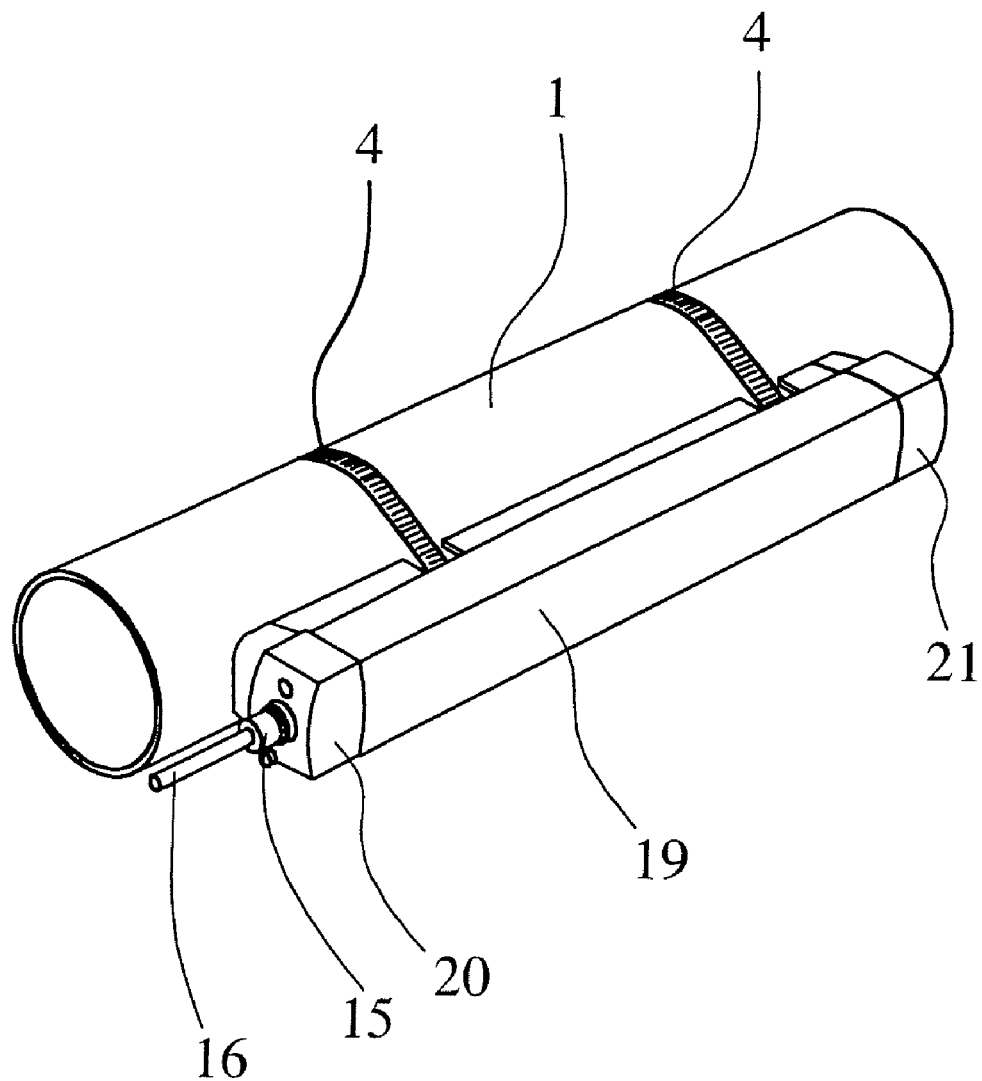
FIG. 5 is a perspective view of the ultrasonic flow rate measuring device according to the second preferred embodiment of the invention in the completely assembled state.

In the ultrasonic flow rate measuring device according to a second preferred embodiment of the invention which is shown in FIGS. 3 to 5, essentially the same structure is provided as described above. However, in addition, there is an electrical connecting box 12 here. This electrical connecting box 12 has two connections 13 which lead via a respective cable 14 to each of the ultrasonic transducers 2. Moreover, the electrical connecting box has a connection 15 which leads via a cable 16 to the measurement device electronics (not shown). The electrical connecting box 12 is made such that it has a plug-in connection 17 which can be easily detached in order to then be able to easily unclamp the entire ultrasonic flow rate measuring device according to the second first preferred embodiment of the invention described here from the line 1.

As is especially apparent from FIGS. 3 & 4, the electrical connecting box 12 is made in two parts, the first part 18 being attached directly to the guide frame 3. Afterwards, when the ultrasonic flow rate measuring device according to the second preferred embodiment of the invention is assembled, the device cover 19 is put in place before the second part 20 of the electrical connecting box 12 is attached laterally to the ultrasonic flow rate measuring device and is screwed to the first part 18 so that the device cover 19 is closed laterally. On the opposite end, the device cover 19 is closed by a corresponding cap 21 (FIG. 5) without a cable penetration.

Thus, an ultrasonic flow rate measuring device is achieved which is also easy to handle with respect to its cabling, in which specifically there is very little danger that one of the cables 13, 14, 16 will be damaged when the ultrasonic flow rate measuring device is installed or removed from the line 1.

What is claimed is:

1. Ultrasonic flow rate measuring device for measuring the flow rate through a line through which a medium flows, comprising:
   at least one ultrasonic transducer,
   a guide frame for guiding and holding the ultrasonic transducer, and
   an electrical connecting box which has a connection for electrical connection of a cable to the ultrasonic transducer and a connection for electrical connection of another cable to the measuring device electronics;
   wherein a respective plug-in connection is provided for the connection for a cable to the ultrasonic transducer and for the connection for the cable to the measuring device electronics.

2. Ultrasonic flow rate measuring device in accordance with claim 1, wherein the cable to the ultrasonic transducer runs within the guide frame.

3. Ultrasonic flow rate measuring device in accordance with claim 1, wherein the electrical connecting box is attached to the guide frame.

4. Ultrasonic flow rate measuring device in accordance with claim 1, wherein there are two ultrasonic transducers.

5. Ultrasonic flow rate measuring device in accordance with claim 1, further comprising means for clamp-on attachment of the measuring device to a line through which flows a medium the flow rate of which is to be measured.

6. Ultrasonic flow rate measuring device in accordance with claim 5, wherein said at least one ultrasonic transducer is mounted for lateral movement along the guide frame and wherein clamping means is provided for fixing the at least one ultrasonic transducer at the position to which it has been moved independent of whether or not the measuring device is attached to a line through which flows a medium the flow rate of which is to be measured.

7. Ultrasonic flow rate measuring device in accordance with claim 6, wherein said at least one ultrasonic transducer comprises two ultrasonic transducers which are independently laterally adjustable relative to each other.

8. Ultrasonic flow rate measuring device in accordance with claim 6, wherein said at least one ultrasonic transducer is mounted for movement in directions corresponding to movement toward and away from a line through which flows a medium the flow rate of which is to be measured in an installed state of the measuring device, and wherein said clamping means is compressed for securing of the lateral position of the ultrasonic transducer when the ultrasonic transducer is moved in a direction corresponding to said movement toward the line and is uncompressed so as to release the ultrasonic transducer for lateral movement when the ultrasonic transducer is moved in a direction corresponding to said movement toward the line.

9. Ultrasonic flow rate measuring device in accordance with claim 8, further comprising means for limiting contact pressure between said at least one ultrasonic transducer the line through which flows a medium the flow rate of which is to be measured in an installed state of the measuring device, the means for limiting contact pressure being incorporated into an adjustment mechanism which is operative for both producing said movement in directions corresponding to movement toward and away from a line through which flows a medium the flow rate of which is to be measured in an installed state of the measuring device and for producing of said clamping means.

10. Ultrasonic flow rate measuring device for measuring the flow rate through a line through which a medium flows, comprising:
   at least one ultrasonic transducer,
   a guide frame for guiding and holding the ultrasonic transducer, and an electrical connecting box which has a connection for electrical connection of a cable to the ultrasonic transducer and a connection for electrical connection of another cable to the measuring device electronics;

wherein the electrical connecting box is made of two parts, a first of said parts being attached directly to the guide frame laterally covered by a device cover, and wherein a second part of the two parts of the electrical connecting box is attached to the first part in a manner closing the device cover at one end.

* * * * *